US006627748B1

(12) United States Patent
Ju et al.

(10) Patent No.: US 6,627,748 B1
(45) Date of Patent: Sep. 30, 2003

(54) COMBINATORIAL FLUORESCENCE ENERGY TRANSFER TAGS AND THEIR APPLICATIONS FOR MULTIPLEX GENETIC ANALYSES

(75) Inventors: Jingyue Ju, Englewood Cliffs, NJ (US); Zengmin Li, New York, NY (US); Anthony Tong, New York, NY (US); James J. Russo, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 37 days.

(21) Appl. No.: 09/658,077

(22) Filed: Sep. 11, 2000

(51) Int. Cl.[7] .................. C07H 21/00; C07H 21/04; C12Q 1/68; G01N 33/53; G01N 33/543

(52) U.S. Cl. .................. 536/25.32; 435/4; 435/6; 435/7.1; 435/DIG. 41; 435/91.1; 436/501; 436/518; 536/23.1; 536/24.3; 530/323; 530/345

(58) Field of Search .................. 435/4, 6, 7.1, DIG. 41, 435/91.1; 436/501, 518; 536/23.1, 24.3, 25.32; 530/323, 345

(56) References Cited

U.S. PATENT DOCUMENTS

| | | | |
|---|---|---|---|
| 4,824,775 A | | 4/1989 | Dattagupta et al. |
| 5,118,605 A | | 6/1992 | Urdea |
| 5,174,962 A | | 12/1992 | Brennan |
| 5,302,509 A | | 4/1994 | Cheeseman |
| 5,654,419 A | | 8/1997 | Mathies et al. |
| 5,728,528 A | * | 3/1998 | Mathies et al. ............... 435/6 |
| 5,770,367 A | | 6/1998 | Southern |
| 5,804,386 A | | 9/1998 | Ju |
| 5,814,454 A | | 9/1998 | Ju |
| 5,834,203 A | | 11/1998 | Katzir et al. |
| 5,853,992 A | * | 12/1998 | Glazer et al. ............... 435/6 |
| 5,869,255 A | * | 2/1999 | Mathies et al. ............... 435/6 |
| 5,876,936 A | | 3/1999 | Ju |
| 5,945,283 A | | 8/1999 | Kwok et al. |
| 5,952,180 A | | 9/1999 | Ju |
| 6,028,190 A | * | 2/2000 | Mathies et al. ............ 536/26.6 |
| 6,046,005 A | | 4/2000 | Ju |
| 6,218,118 B1 | | 4/2001 | Sampson et al. |
| 6,316,230 B1 | | 11/2001 | Egholm et al. |

FOREIGN PATENT DOCUMENTS

| | | |
|---|---|---|
| WO | WO0222883 | 3/2002 |
| WO | WO02079519 | 4/2002 |
| WO | WO0229003 | 10/2002 |

OTHER PUBLICATIONS

Hacia J. G., Edgemon K., Sun B., Stern D., Fodor S.A., Collins F.S. (1998). Two Color Hybridization Analysis Using High Density Oligonucleotide Arrays and Energy Transfer Dyes. Nucleic Acids Res. 26:3865–6. (Exhibit H).

Ju, J., Glazer, A. N. and Mathies, R.A. (1996) Cassette Labeling for facile construction of energy transfer flourescent primers. Nucleic Acids Res. 24: 114–1148. (Exhibit I).

Ju, J., Glazer, A. N. and Mathies, R.A. (1996) Energy transfer primers: A new fluorescence labeling paradigm for DNA sequencing and analysis. Nature Medicine 2: 246–249. (Exhibit J).

Ju, J., Ruan C., Fuller, C.W., Glazer, A. N. and Mathies, R.A. (1995) Fluorescence energy transfer dye–labeled primers for DNA sequencing and analysis. Proc. Natl. Acad. Sci. USA 92: 4347–4351. (Exhibit K).

Lee, L.G., Spurgeon, S.L., Heiner, C.R., Benson, S.C., Rosenblum, B.B., Menchen, S.M., Graham, R.J., Constantinescu, A., Upadhya, K.G. and Cassel, J.M. (1997) New energy transfer dyes for DNA sequencing. Nucleic Acids Res. 25: 2816–2822. (Exhibit L).

Speicher, M. R., Ballard, S.G. and Ward, D.C. (1996) Karyotyping human chromosomes by combinatorial multi–fluor Fish. Nature Genetics 12: 368–375 (Exhibit M).

Benson, S. C., Mathies, R. A. and Glazer, A. N. (1993). Heterodimeric DNA–binding dyes designed for energy transfer: stability and applications of the DNA complexes. Nucleic Acids Res. 21: 5720–5726. (Exhibit E).

Benson, S. C., Singh, P. and Glazer, A. N. (1993). Heterodimeric DNA–binding dyes designed for energy transfer: synthesis and spectroscopic properties. Nucleic Acids Res. 21: 5727–5735. (Exhibit F).

Chen, X. and Kwok, P.–Y. (1997) Template–directed dye–terminator incorporation (TDI) assay: a homogeneous DNA diagnostic method based on fluorescence resonance energy transfer Nucleic Acids Res. 25: 347–353. (Exhibit G).

Monforte J.A., Becker C.H., High–throughput DNA analysis by time–of–flight mass spectrometry. Nat. Med. 3(3):360–362 (1997).

Roskey M.T, Juhasz P., Smirnov I.P., Takach E.J., Martin S.A., Haff L.A., DNA sequencing by delayed extraction–matrix–assisted laser desorption/ionization time of flight mass spectrometry. Proc. Natl. Acad. Sci. USA. 93:4724–4729 (1996).

Tang K., Fu D.J., Julien D., Braun A., Cantor C.R., Koster H., Chip–based genotyping by mass spectrometry. Proc. Natl. Acad. Sci. USA. 96:10016–10020 (1999).

(List continued on next page.)

Primary Examiner—Maurie Garcia Baker
(74) Attorney, Agent, or Firm—John P. White

(57) ABSTRACT

This invention provides a combinatorial fluorescence energy transfer tag which comprises a plurality of fluorescent molecules, comprising one or more energy transfer donor and one or more energy transfer acceptor, linked through a molecular scaffold wherein the fluorescent molecules are separated along the scaffold to produce a unique fluorescence emission signature. The invention further provides for the use of said tags in multi-component analyses, including multiplex genetic analyses.

3 Claims, 10 Drawing Sheets

OTHER PUBLICATIONS

Tong X. and Smith L.M., Solid–Phase Method for the Purification of DNA Sequencing Reactions. *Anal. Chem.* 64: 2672–2677 (1992); and.

Olejnik J. et al. (1995) Photocleavable biotin derivatives: a versatile approach for the isolation of biomolecules. *Proc. Natl. Acad. Sci. USA.* 92:7590–7954.

Woolley, A. T. et al. (1997) High–Speed DNA Genotyping Using Microfabricated Capillary Array Electrophoresis Chips. *Anal. Chem.* 69:2181–2186.

Fei, Z. et al. (1998) MALDI–TOF mass spectrometric typing of single nucleotide polymorphisms with mass–tagged ddNTPs. Nucleic Acids Research 26(11):2827–2828.

Olejnik, J. et al (1999) Photocleavable peptide–DNA conjugates: synthesis and applications to DNA analysis using MALDI–MS. *Nucleic Acids Res.* 27(23):4626–4631.

Arbo et al., Solid Phase Synthesis of Protected Peptides Using New Cobalt (III) Amine Linkers, *Int. J. Peptide Protein Res.* (1993) 42:138–154.

Bergseid M., Baytan A.R., Wiley J.P., Ankener W.M., Stolowitz, Hughs K.A., Chestnut J.D., Small–molecule base chemical affinity system for the purification of proteins. *BioTechniques* 29:1126–1133 (2000).

Chiu N.H., Tang K., Yip P., Braun A., Koster H., Cantor C.R., Mass spectrometry of single–stranded restriction fragments captured by an undigested complementary sequence. *Nucleic Acids Res.* 28:E31 (2000).

Fu D.J., Tang K., Braun A., Reuter D., Darnhofer–Demar B., Little D.P., O'Donnell M.J., Cantor C.R., Koster H., Sequencing exons 5 to 8 of the p53 gene by MALDI–TOF mass spectrometry. *Nat. Biotechnol.* 16:381–384 (1998).

Jurinke C., van de Boom D., Collazo V., Luchow A., Jacob A, Koster H., Recovery of nucleic acids from immobilized biotin–streptavidin complexes using ammonium hydroxide and application in MALDI–TOF mass spectrometry. *Anal. Chem.* 69: 904–910 (1997).

Pelletier H., Sawaya M.R., Kumar A., Wilson S.H., Kraut J. (1994) Structures of ternary complexes of rat DNA polymerase β, a DNA template–primer, and ddCTP. *Science* 264: 1891–1903.

Prober J.M., Trainor G.L., Dam R.J., Hobbs F.W., Robertson C.W., Zagursky R.J., Cocuzza A.J., Jensen M.A., Baumeister K. (1987) A system for rapid DNA sequencing with fluorescent chain–terminating dideoxynucleotides. *Science* 238: 336–341.

Ronaghi M., Uhlen M., Nyren P. (1998) A sequencing Method based on real–time pyrophosphate. *Science* 281: 364–365.

Rosenblum, B.B. et al. (1997) New dye–labeled terminators for improved DNA sequencing patterns. *Nucleic Acids Res.* 25: 4500–4504.

Ross, P. et al. (1998) High Level Multiplex Genotyping by MALDI–TOF Mass Spectrometry. *Nat. Biotech.* 16:1347–1351.

Ross, P.L. et al. (1997) Discrimination of Single–Nucleotide Polymorphisms in human DNA Using Peptide Nucleic Acid Probes Detected by MALDI–TOF Mass Spectrometry. *Anal. Chem.* 69:4197–4202.

Saxon E. and Bertozzi C.R. (2000) Cell surface engineering by a mofified Staudinger reaction. *Science* 287: 2007–2010.

Schena M., Shalon D., Davis, R. Brown, P.O. (1995) Quantitative monitoring of gene expression patterns with a complementary DNA microarray. *Science* 270: 467–470.

Stoerker J. et al. (2000) Rapid Genotyping by MALDI–monitored nuclease selection from probe libraries. *Nat. Biotech.* 18:1213–1216.

Welch M.B., Burgess K. (1999) Synthesis of fluorescent, photolabile 3'–O–protected nucleoside triphosphates for the base addition sequencing scheme. *Nucleosides and Nucleotides* 18:197–201.

Hyman E.D. (1988) A new method of sequencing DNA. *Analytical Biochemistry* 174: 423–436.

Ireland R.E., and Varney M.D. (1986) Approach to the total synthesis of chlorothricolide—synthesis of (+/–)–19.20–dihydro –24–O–methylchlorothricolide, methyl–ester, ethyl carbonate. *J. Org. Chem.* 51: 635–648.

Jiang–Baucom, P. et al. (1991) DNA Typing of Human Leukocyte Antigen Sequence Polymorphisms by Peptide Nucleotide Acid Probes and MALDI–TOF Mass Spectrometry. *Anal Chem.* 69:4894–4896.

Kamal A., Laxman E. Rao N.V. (1999) A mild and rapid regeneration of alcohols from their allylic ethers by chlorotrimethylsilane/sodium iodide. *Tetrahedron Lett.* 40: 371–372.

Lee, L.G., et al. (1992) DNA sequencing with dye–labeled terminators and T7 DNA polymerase: effect of dyes and dNTPs on incorporation of dye terminators and probability analysis of termination fragments. *Nucleic Acids Res.* 20: 2471–2483.

Li, J., (1999) Single Oligonucleotide Polymorphism Determination Using Primer Extension and Time–of–Flight Mass Spectrometry. *Electrophoresis,* 20:1258–1265.

Liu, H. et al., (2000) Development of Multichannel Devices with an Array of Electrospray Tips for High–Throughput Mass Spectrometry. *Anal. Chem.* 72:3303–3310.

Lyamichev, A. et al. (1999) Polymorphism Identification and Quantitative Detection of Genomic DNA by Invasive Cleavage of Oligonucleotide Probes. *Nat. Biotech.* 17:292–296.

Metzker M.L., et al. (1994) Termination of DNA synthesis by novel 3'–modified deoxyribonucleoside 5'–triphosphates. *Nucleic Acids Res.* 22:4259–4267.

Chen, X. and Kowk, P.–Y. (1997) Template–directed dye–terminator incorporation (TDI) assay: a homogeneous DNA diagnostic method based on fluorescence resonance energy transfer. *Nucleic Acids Res.* 25: 347–353.

Hacia J.G., Edgemon K., Sun B., Stern D., Fodor S.A., Collins F.S. (1998) Two Color Hybridization Analysis Using High Density Oligonucleotide Arrays and Energy Transfer Dyes. *Nucleic Acids Res.* 26: 3865–6.

Ju, J., Glazer, A.N. and Mathies, R.A. (1996) Energy transfer primers: A new fluorescence labeling paradigm for DNA sequencing and analysis. *Nature Medicine* 2: 246–249.

U.S. Application Serial No. 09/823,181, filed Mar. 30, 2001, Ju et al.

U.S. Application Serial No. 10/194,882, filed Mar. 30, 2001, Ju et al.

U.S. Application Serial No. 09/972,364, filed Oct. 5, 2001, Ju et al.

U.S. Application Serial No. 09/684,670, filed Oct. 6, 2001, Ju et al.

Axelrod V.D., et al. (1978) Specific termination of RNA polymerase synthesis as a method of RNA and DNA sequencing. *Nucleic Acids Res.* 5(10):3549–3563.

Badman, E. R. et al. (2000) A Parallel Miniature Cylindrical Ion Trap Array. *Anal. Chem.* 72:3291–3297.

Badman, E. R. et al. (2000) Cylindrical Ion Trap Array with Mass Selection by Variation in Trap Dimensions. *Anal. Chem.* 72:5079–5086.

Burgess, K. et al. (1997) Photolytic Mass Laddering for Fast Characterization of Oligomers on Single Resin Beads. *J. Org. Chem.* 62:5662–5663.

Canard B., et al. (1995) Catalytic editing properties of DNA polymerases. *Proc. Natl. Acad. Sci. USA* 92: 10859–10863.

Caruthers M.H. (1985) Gene synthesis machines: DNA chemistry and its uses. *Science* 230: 281–285.

Chee M., et al. (1996) Accessing genetic information with high-density DNA arrays. *Science* 274: 610–614.

Edwards, J. et al. (2001) DNA sequencing using biotinylated dideoxynucleotides and mass spectrometry. *Nucleic Acids Res.* 29(21):e104.

Griffin, T.J. et al. (1999) Direct Genetic Analysis by Matrix-Assisted Laser Desorption/Ionization Mass Spectrometry. *Proc. Nat. Acad. Sci. USA* 96:6301–6306.

Haff L.A., et al. (1997) Multiplex Genotyping of PCR Products with Mass Tag-Labeled Primers. *Nucleic Acids Res.* 25(18):3749–3750.

* cited by examiner

* This proline derivative can be prepared from acrylonitrile derivative and diethyl malonate according to the published literature. Vogel's Textbook of Practical Organic Chemistry, 1989, Fifth Edn. p. 758 Longman A: Normal Chromosome B: Chromosome with marker 2 deleted (Deletion)

C: Chromosome with 2 copies of marker 3 (Expansion)

Representative Example of CFET Tags

| CFET Tag | Fluorescence Signature | Tag ID |
|---|---|---|
|  |  525 nm | 1 |
|  |  525 nm  580 nm | 2 |
|  |  525 nm  580 nm | 3 |
|  |  525 nm  580 nm | 4 |
|  |  525 nm  580 nm | 5 |
|  |  525 nm  670 nm | 6 |
|  |  525 nm  670 nm | 7 |
|  |  525 nm  670 nm | 8 |
|  |  525 nm  580 nm  670 nm | 9 |
|  |  525 nm  580 nm  670 nm | 10 |

SEQUENCE LISTING

<160> NUMBER OF SEQ ID NOS: 17

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: scaffold

<400> SEQUENCE: 1
tttttttttt tttttttttt tttttc                                        26

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 2
ttaaaaagaa taagggtgtc                                               20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 3
acatagccga tcggatagag                                               20

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: primer

```
<400> SEQUENCE: 4
tcatagccga tcggatagag gc                                              22

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 5
acatagccga tcggatagag                                                 20

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 6
gccgatttat gtgaaacact tgcg                                            24

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 7
accgatttat gtgaaacact tgcgga                                          26

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 8
cggaagacag actcgtgggt                                                 20

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 9
cttaatcttg tatagtagac ctgggaaa                                        28

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 10
attaatcttg tatagtagac ctgggaaaag                                      30
```

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 11
atagtagacc tgggaaaagg                                          20

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 12
tcgtgtggga cgtcttactc atacttgagt                               30

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 13
gcgtgtggga cgtcttactc atacttgagt ac                            32

<210> SEQ ID NO 14
<211> LENGTH: 100
<212> TYPE: DNA
<213> ORGANISM: Artificial Sequence
<220> FEATURE:
<223> OTHER INFORMATION: Description of Artificial Sequence: template

<400> SEQUENCE: 14
gtaaaaatga ctaattttc ttattcccac agtgtatcgg ctagcctatc tccggctaaa      60
tacactttgt gaacgccttc tgtctgagca cccagaatta                          100

<210> SEQ ID NO 15
<211> LENGTH: 100
<212> TYPE: DNA
<213> ORGANISM: Artificial Sequence
<220> FEATURE:
<223> OTHER INFORMATION: Description of Artificial Sequence: template

<400> SEQUENCE: 15
gtaaaaatga ctaattttc ttattcccac agagtatcgg ctagcctatc tctggctaaa     60
tacactttgt gaacgccttc tgtctgagca cccagaatta                          100

<210> SEQ ID NO 16
<211> LENGTH: 100
<212> TYPE: DNA
<213> ORGANISM: Artificial Sequence
<220> FEATURE:
<223> OTHER INFORMATION: Description of Artificial Sequence: template

<400> SEQUENCE: 16
tacactttgt gaacgccttc tgtctgagca cccagaatta gaacatatca tctggaccct    60
tttccagcac accctgcaga atgagtatga actcatgaga                         100

```
<210> SEQ ID NO 17
<211> LENGTH: 100
<212> TYPE: DNA
<213> ORGANISM: Artificial Sequence
<220> FEATURE:
<223> OTHER INFORMATION: Description of Artificial Sequence: template

<400> SEQUENCE: 17
tacactttgt gaacgccttc tgtctgagca cccataatta gaacatatca tctggaccct      60
tttcccgcac accctgcaga atgagtatga actcatgaga                          100
```

COMBINATORIAL FLUORESCENCE ENERGY TRANSFER TAGS AND THEIR APPLICATIONS FOR MULTIPLEX GENETIC ANALYSES

BACKGROUND OF THE INVENTION

Throughout this application, various publications are referenced in parentheses by author and year. Full citations for these references may be found at the end of the specification immediately preceding the claims. The disclosures of these publications in their entireties are hereby incorporated by reference into this application to more fully describe the state of the art to which this invention pertains.

The need to study many biological targets simultaneously drives the development of multiplex fluorescent tags. However, due to the limits of the spectral region, and therefore the availability of appropriate detectors, the number of available fluorescent dyes that have distinguishable emission spectra is limited to about ten. To overcome this limitation, a combinatorial fluorescent labeling approach for multi-color fluorescence in situ hybridization (M-FISH) has been developed and is now widely used in the field of cytogenetics (Speicher et al., 1996; Schrock et al., 1996). This approach mixes from two to seven individual fluorescent dyes that have unique emissions, and uses the fluorescence emission pattern to identify the different targets. The unique fluorescence emission pattern is achieved by mathematically combining the different dyes. This development has made possible advances in chromosome analyses. However, the procedure requires physically mixing the individual dyes in a quantitative manner to develop "unique" probe labels. This requirement, coupled with the potential interactions of the dyes, complicates the fluorescence emission patterns. Therefore, the major application of the technique is limited to methods that involve hybridization. Multiple lasers and detectors are also required for the imaging. A reagent kit that can be used to covalently label a wide range of biomolecules is difficult to construct with this approach. Thus, there is an urgent need for a large set of fluorescent tags that can be used for multiple component analyses in biomedical and other fields. Previously, the principle of fluorescent energy transfer (ET) was used to enhance fluorescence emission for the successful development of four ET tags for deoxyribonucleic acid (DNA) sequencing which are widely used in the Human Genome Project (Ju et al. 1995, 1996).

The present application discloses how energy transfer and combinatorial concepts can be used to tune the fluorescence emission signatures of the fluorescent tags for the development of a large number of combinatorial fluorescence energy transfer (CFET) tags. All the CFET tags can be excited with a single laser source and analyzed by simple detectors. Such CFET tags should be valuable for multiplex genetic mutation analysis, DNA mapping, and genome-wide chromosome analysis, as well as for other multi-component analysis systems.

SUMMARY OF THE INVENTION

This invention is directed to a combinatorial fluorescence energy transfer tag which comprises a plurality of fluorescent molecules, comprising one or more energy transfer donor and one or more energy transfer acceptor, linked through a molecular scaffold wherein the fluorescent molecules are separated along the scaffold to produce a unique fluorescence emission signature.

The invention provides a combinatorial fluorescence energy transfer tag which comprises the structure:

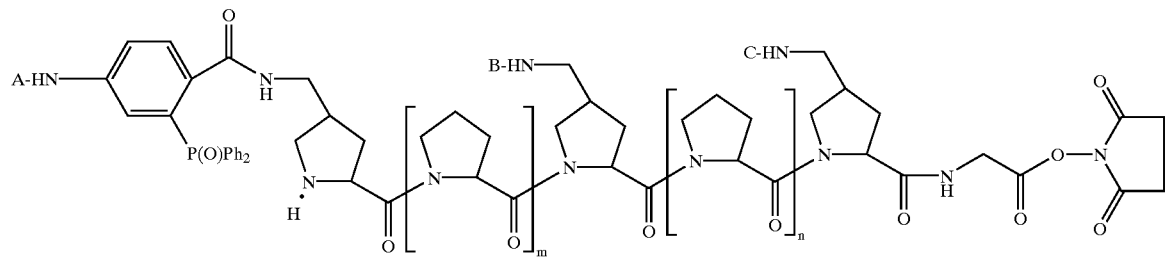

wherein A, B, and C represent different fluorescent molecules which comprise one or more energy transfer donor and one or more energy transfer acceptor, wherein m and n represent any integer greater than or equal to one, and wherein fluorescent molecules A, B, and C are separated from each other to produce a unique fluorescence emission signature.

The invention provides oligonucleotide primers, oligonucleotide probes, nucleotides, deoxynucleosides, and antibodies labeled with any of the combinatorial fluorescence energy transfer tags disclosed herein.

The invention provides for the use of any of the combinatorial fluorescence energy transfer tags disclosed herein in gene mutation analysis, in mapping nucleic acids, in chromosome analysis, and in binding assays.

The invention provides a plurality of combinatorial fluorescence energy transfer tags comprising any of the combinatorial fluorescence energy transfer tags disclosed herein, wherein each tag in the plurality of tags has a unique fluorescence emission signature.

The numbers in F-4-T-6-C refer to the number of spacing nucleotides in the scaffold between dyes F and T, and T and C. F=Fam; T=Tam; C=Cy5.

Figure 2:
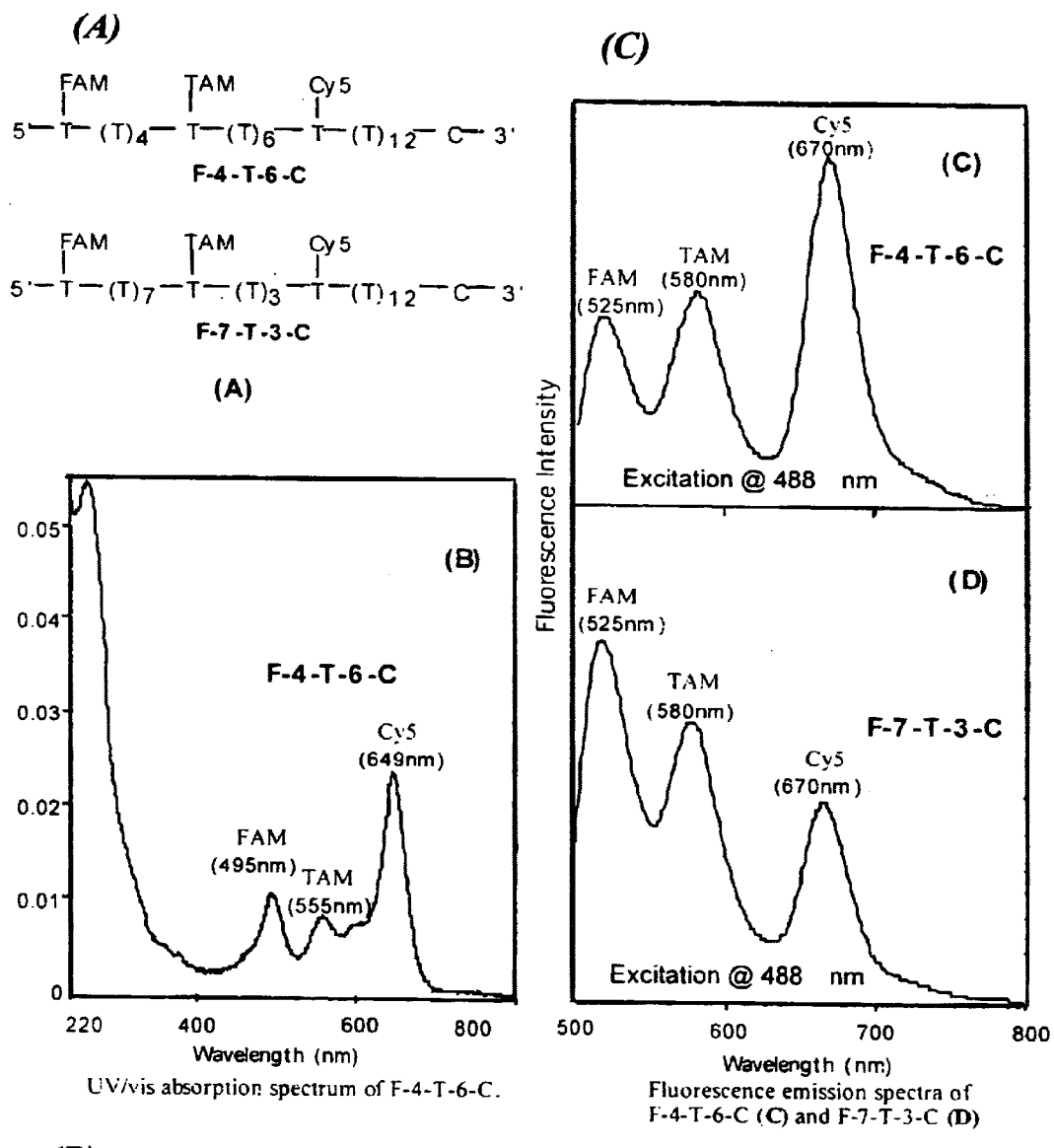

FIG. 2: Spectroscopic data for tags F-4-T-6-C and F-3-T-7-C.

(A) Two tags with different fluorescent signatures have been constructed by varying the spacing between the three dyes F, T, and C.

(B) Ultraviolet/visible (Uv/vis) absorption spectrum of dye F-4-T-6-C.

(C) Fluorescence emission spectra of dye F-4-T-6-C.

(D) Fluorescence emission spectra of dye F-7-T-3-C. F=Fam; T=Tam; C=Cy5.

Figure 3:
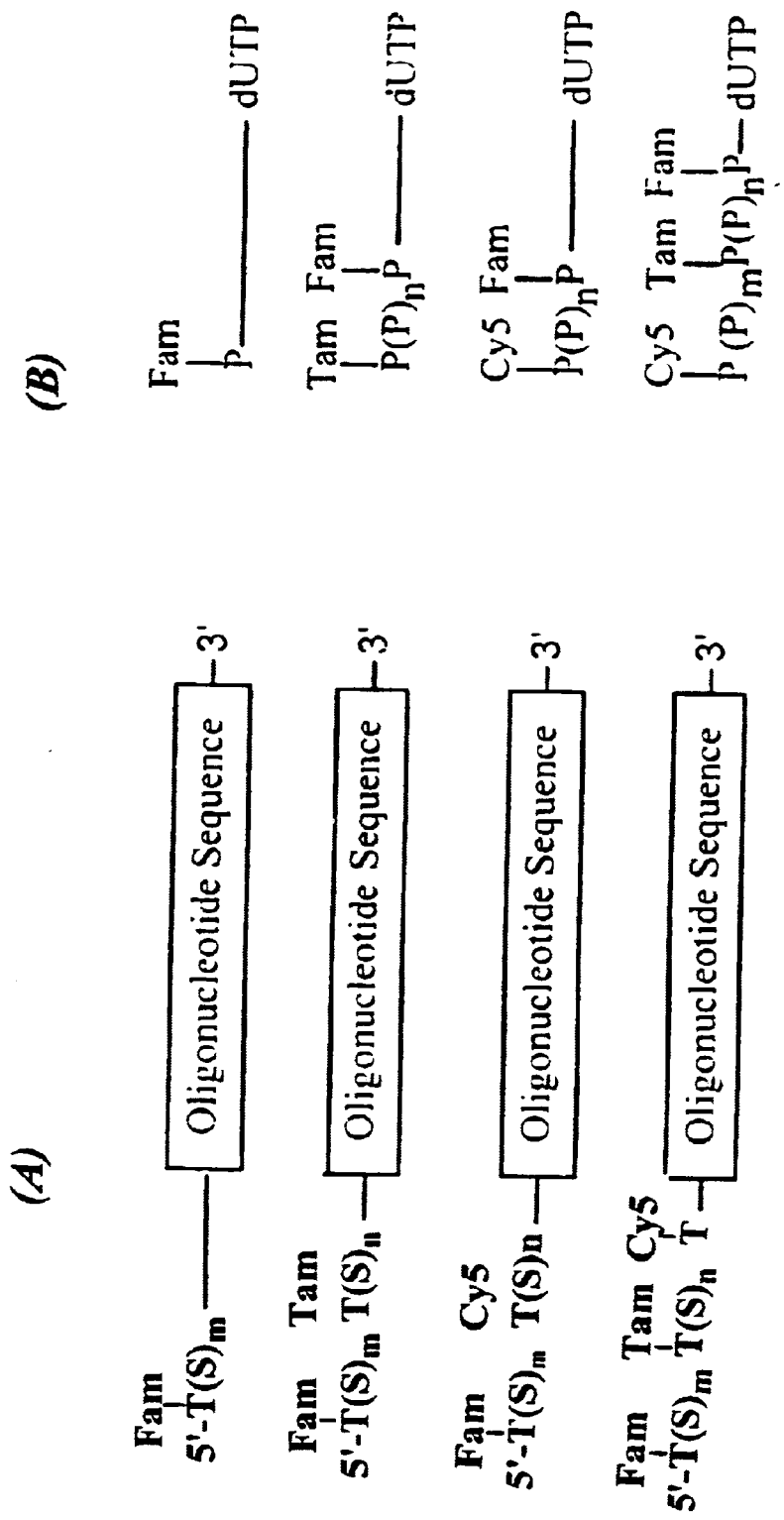

FIG. 3: Schematic labeling approach to construct CFET-primers and CFET-dUTPs.

The spacer between dyes is 1',2'-dideoxyribose phosphate (S) in (A) and proline (P) in (B). "m" and "n" refer to the number of molecules in the spacer. dUTP=deoxyuridine triphosphate.

Figure 4:
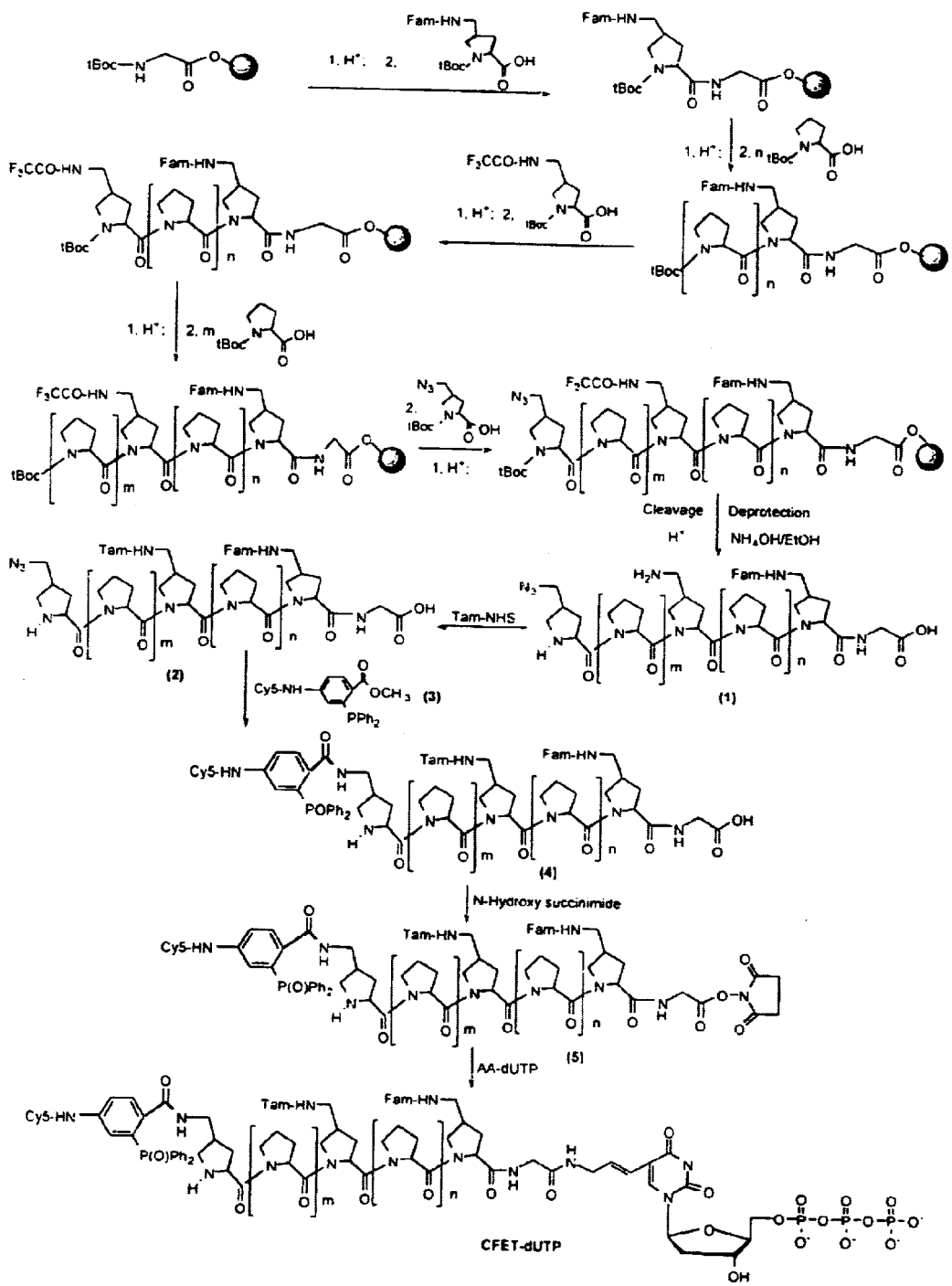

FIG. 4: The synthesis of CFET-dUTP. The CFET tag comprises three different fluorescent dyes: Fam, Tam and Cy5.

Figure 5:
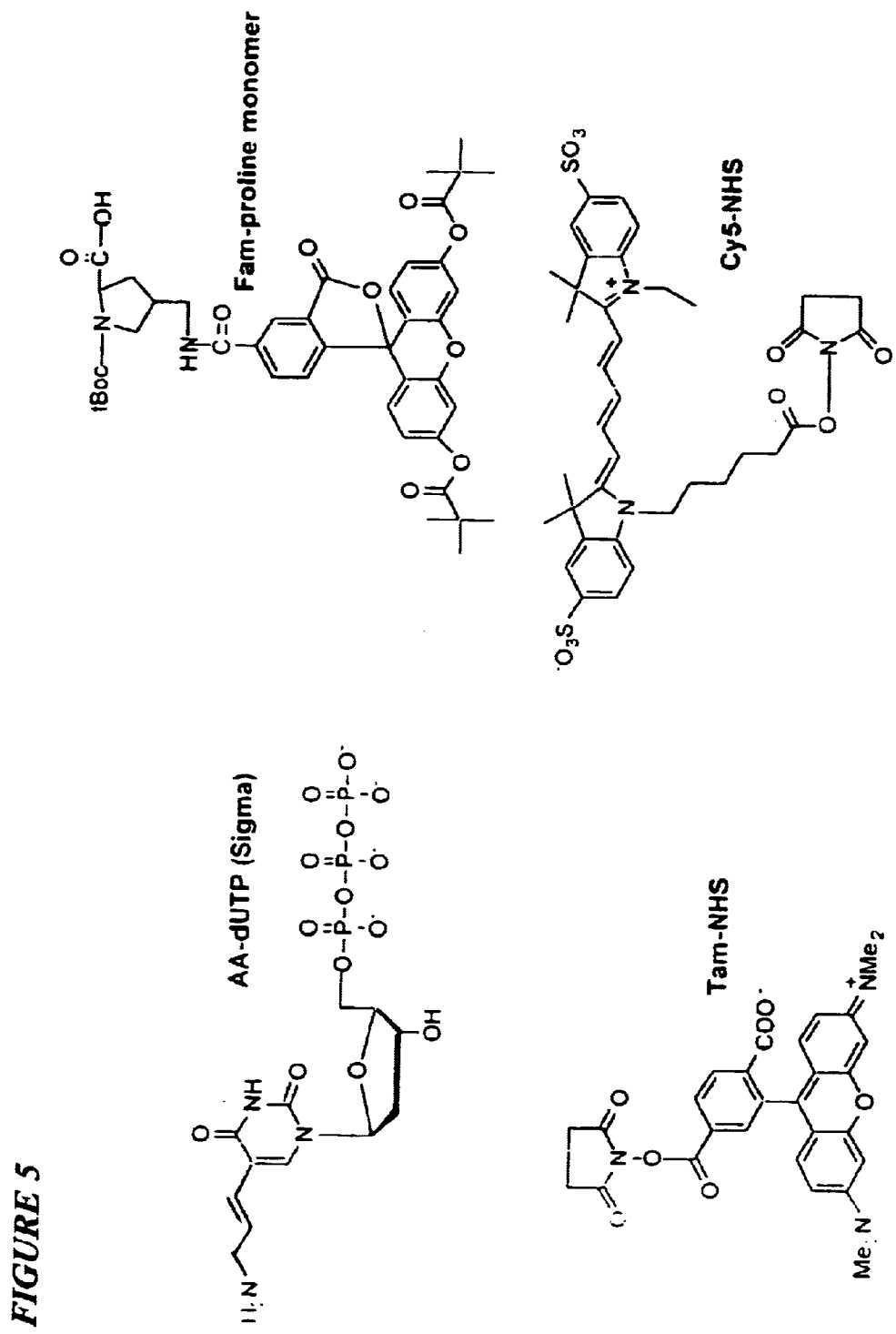

FIG. 5: Structures of Aminoallyl (AA)-dUTP, Fam-proline, and N-Hydroxy succinimide (NHS) esters of TAM and Cy5.

Figure 6:
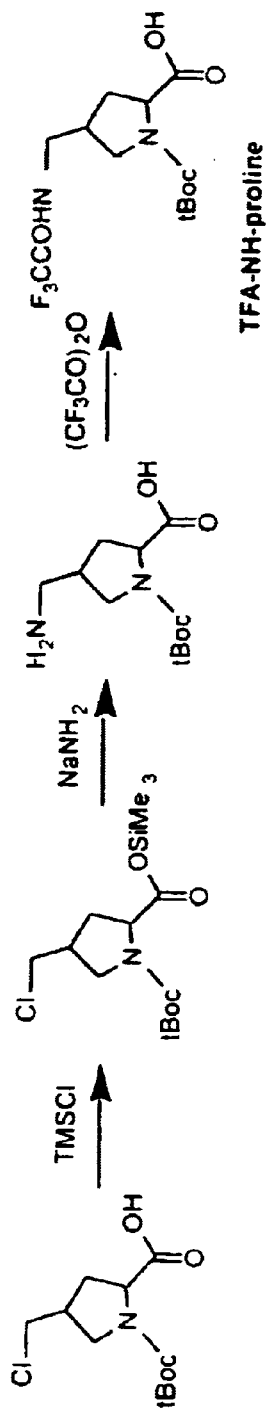
Figure 6:
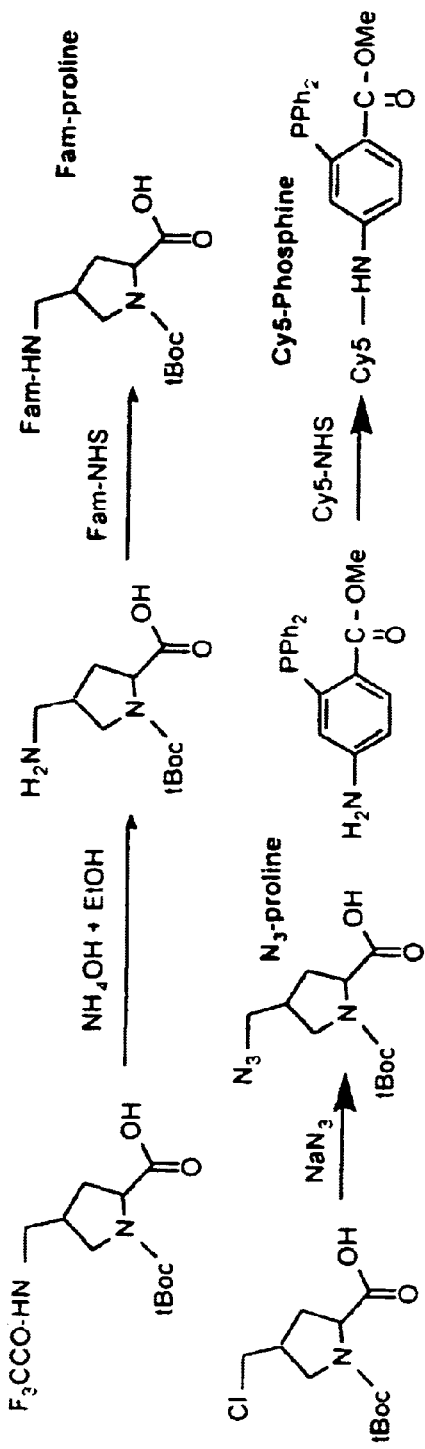

FIG. 6: Synthetic schemes to prepare Fam-proline, Azido-proline and Cy5-phosphine. TMSCl=trimethylsilyl chloride.

Figure 7:
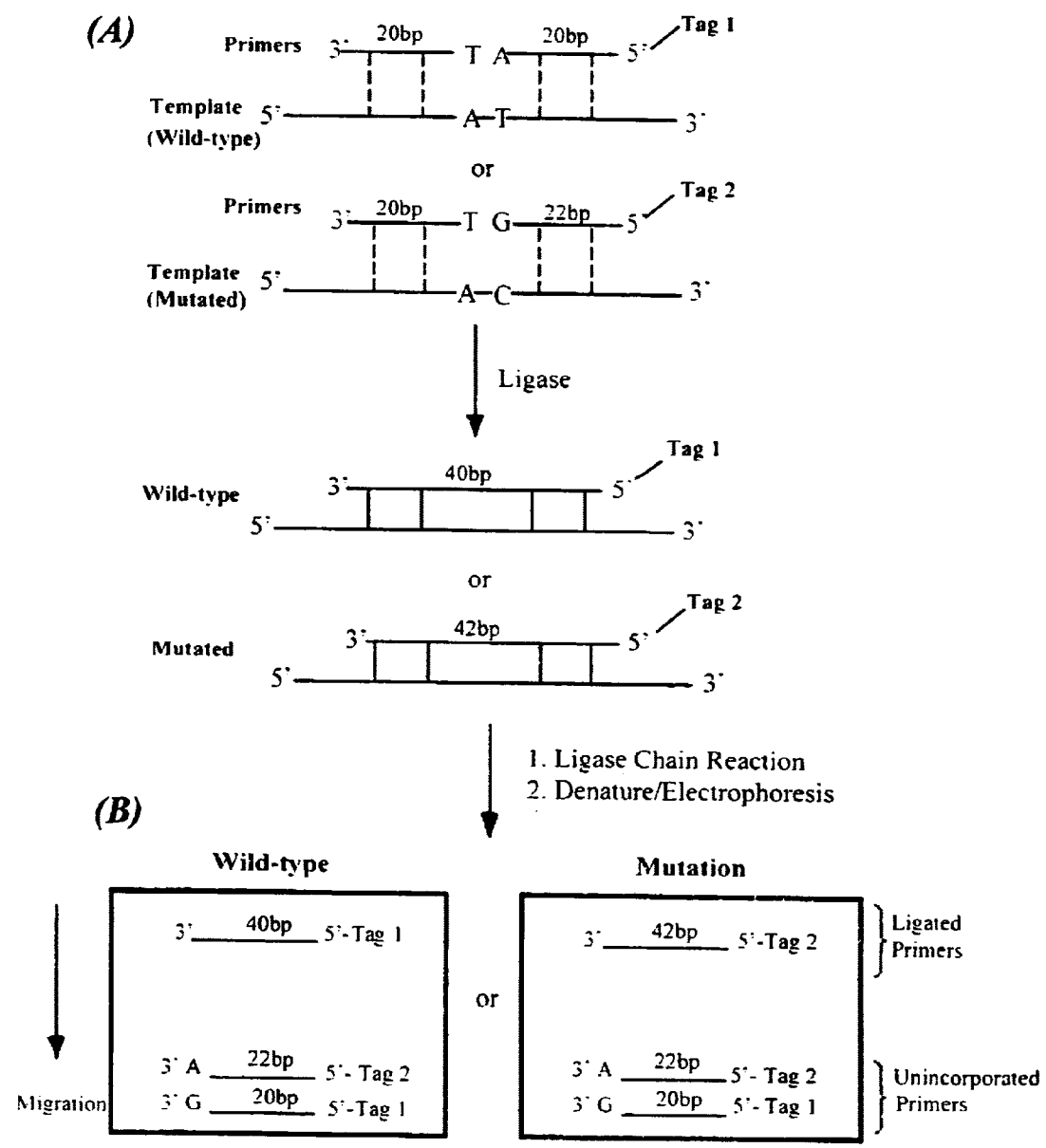

FIG. 7: Schematic using ligase chain reaction for determining the genotype at a locus containing a possible single-base mutation.

(A) Primer pairs are generated surrounding a base that can be mutated. The wild-type primer is labeled with one CFET tag (Tag 1) and the mutation-specific primer with another CFET tag (Tag 2).

(B) Subsequent gel electrophoresis allows separation of ligated primer pairs and unincorporated primers. Different bands appear on the gel depending on whether the template is wild-type or mutated.

Figure 8:
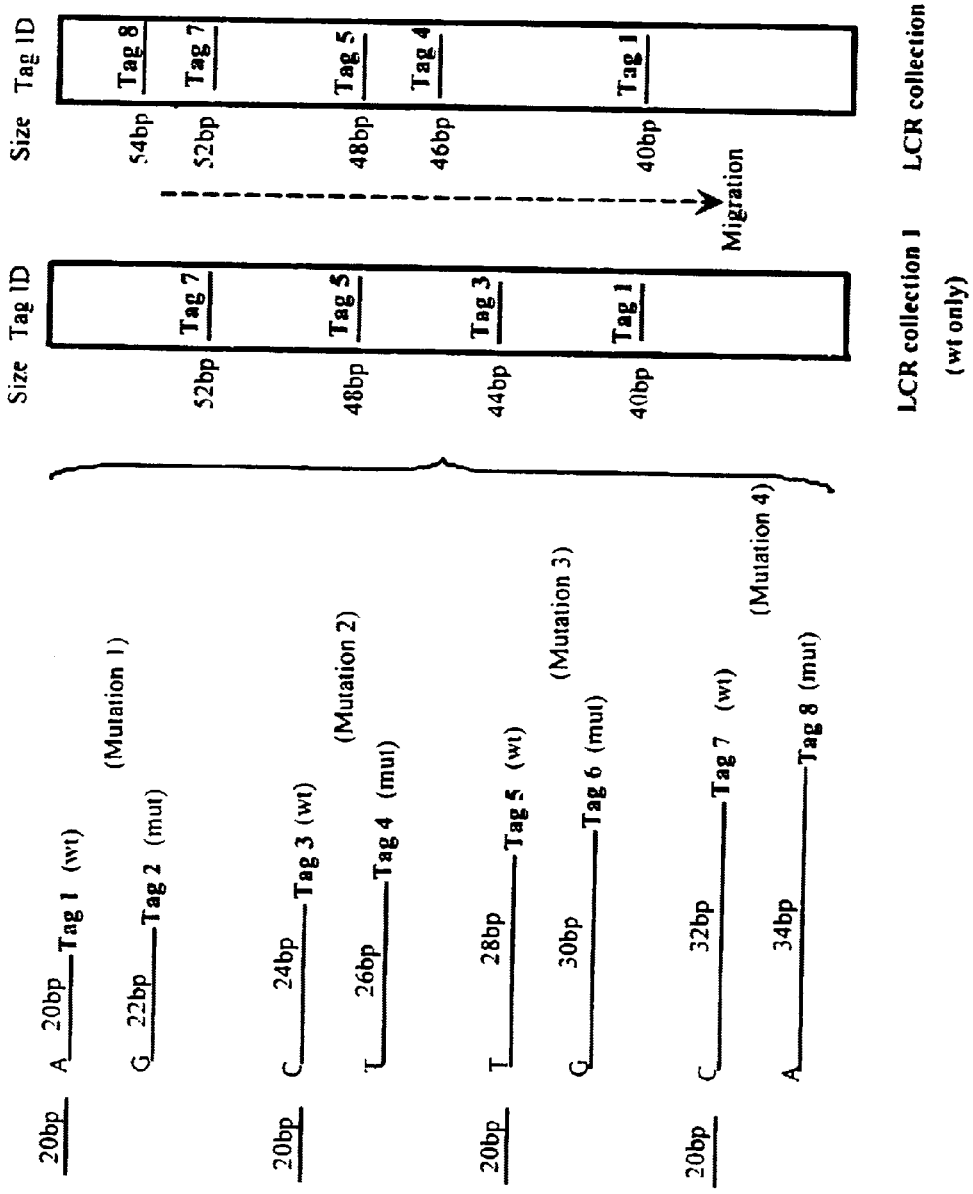

FIG. 8: Schematic of expected results from screening four potential mutation sites of Rb1 gene using eight unique CFET Tags and the ligase chain reaction assay. Only ligation products are shown on the gels.

Figure 9:
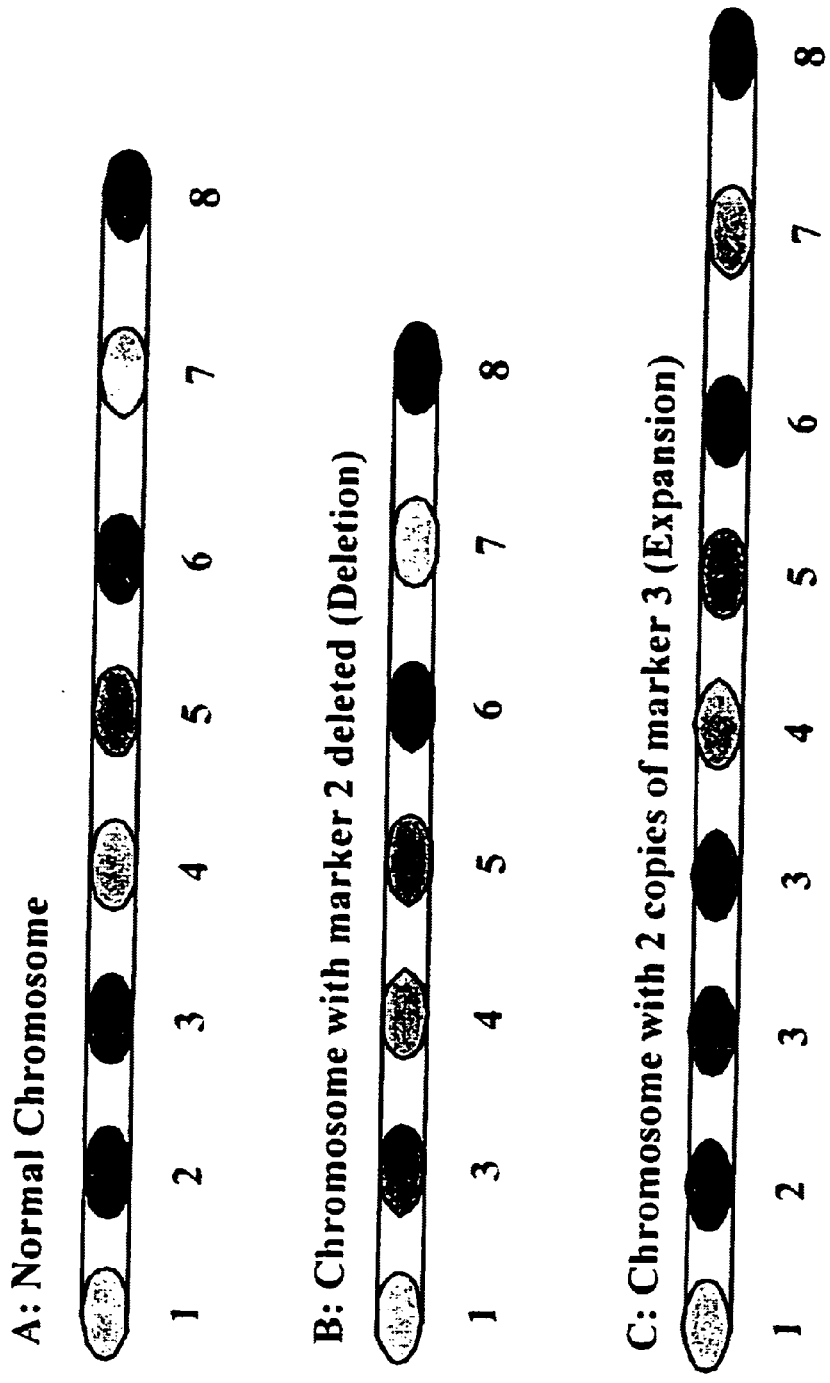

FIG. 9: Schematic of chromosomal studies to detect macrodeletions and amplifications.

Figure 10:
Figure 10:
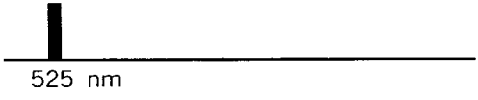
Figure 10:
Figure 10:
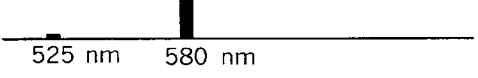
Figure 10:
Figure 10:
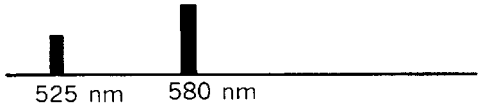
Figure 10:
Figure 10:
Figure 10:
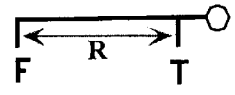
Figure 10:
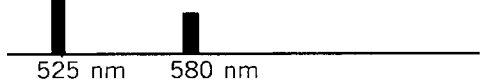
Figure 10:
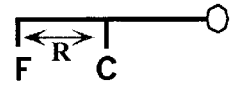
Figure 10:
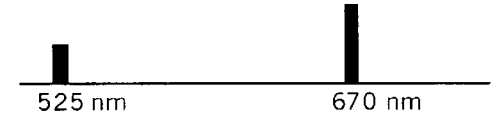
Figure 10:
Figure 10:
Figure 10:
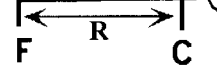
Figure 10:
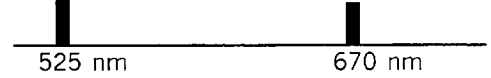
Figure 10:
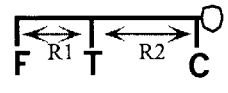
Figure 10:
Figure 10:
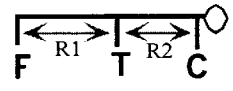
Figure 10:
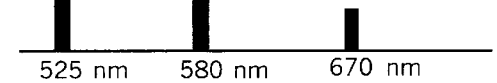

FIG. 10: Representative examples for the construction of the CFET tags and their expected fluorescence signatures.

DETAILED DESCRIPTION OF THE INVENTION

The present invention is directed to a combinatorial fluorescence energy transfer tag which comprises a plurality of fluorescent molecules, comprising one or more energy transfer donor and one or more energy transfer acceptor, linked through a molecular scaffold wherein the fluorescent molecules are separated along the scaffold to produce a unique fluorescence emission signature.

In different embodiments of the invention, the fluorescent molecules are selected from the group consisting of 6-carboxyfluorescein, N,N,N',N'-tetramethyl-6-carboxyrhodamine, and cyanine. In other embodiments, other molecular moieties that are fluorescent are used. In different embodiments, the scaffold comprises molecules selected from the group consisting of nucleotides, dideoxyribose phosphates, dideoxysugar phosphates, and amino acids. In other embodiments, other chemical moieties that are capable of acting as spacers between the fluorescent molecules are used. In one embodiment, the fluorescent molecules are covalently attached to the scaffold. In different embodiments, the combinatorial fluorescence energy transfer tag comprises three or more fluorescent molecules.

The invention provides a combinatorial fluorescence energy transfer tag which comprises the structure:

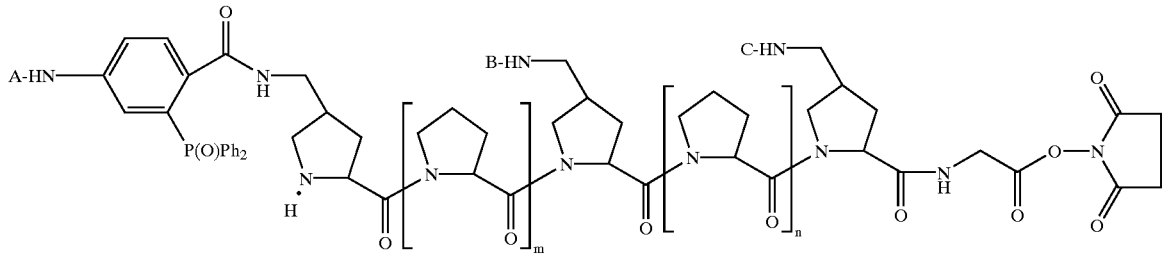

wherein A, B, and C represent different fluorescent molecules which comprise one or more energy transfer donor and one or more energy transfer acceptor, wherein m and n represent any integer greater than or equal to one, and wherein fluorescent molecules A, B, and C are separated from each other to produce a unique fluorescence emission signature. In different embodiments, the fluorescent molecules are selected from the group consisting of 6-carboxyfluorescein, N,N,N',N'-tetramethyl-6-carboxyrhodamine, and cyanine.

The invention provides an oligonucleotide primer labeled using any of the combinatorial fluorescence energy transfer tags disclosed herein. The invention also provides an oligonucleotide probe labeled using any of the combinatorial fluorescence energy transfer tags disclosed herein.

The invention provides a nucleotide labeled using any of the combinatorial fluorescence energy transfer tags disclosed herein. The invention provides a deoxynucleoside labeled using any of the combinatorial fluorescence energy transfer tags disclosed herein. In different embodiments, the deoxynucleoside is selected from the group consisting of deoxyadenosine triphosphate, deoxycytidine triphosphate, deoxyguanosine triphosphate, deoxythymidine triphosphate, and deoxyuridine triphosphate.

The invention provides an antibody labeled using any of the combinatorial fluorescence energy transfer tags disclosed herein. In different embodiments, the antibody is a monoclonal antibody or a polyclonal antibody.

The invention provides for the use of any of the combinatorial fluorescence energy transfer tags disclosed herein in gene mutation analysis. In different embodiments, the gene mutation is associated with disease development. In different embodiments, the disease is cancer, long QT syndrome, immune deficiency/centromeric instability/facial anomalies syndrome, asthma, or diabetes.

The invention provides for the use of any of the combinatorial fluorescence energy transfer tags disclosed herein in mapping nucleic acid. In different embodiments, the nucleic acid is deoxyribonucleic acid (DNA) or deoxyribonucleic (RNA). In different embodiments, the DNA is genomic DNA or cDNA.

The invention provides for the use of any of the combinatorial fluorescence energy transfer tags disclosed herein in chromosome analysis. In one embodiment, the chromosome analysis is a genome wide chromosome analysis.

The invention provides for the use of any of the combinatorial fluorescence energy transfer tags disclosed herein in a binding assay. In different embodiments, the binding assay is a antigen-antibody binding assay or a receptor-ligand binding assay.

The invention provides a plurality of combinatorial fluorescence energy transfer tags comprising any of the combinatorial fluorescence energy transfer tags disclosed herein, wherein each tag in the plurality of tags has a unique fluorescence emission signature. The invention provides a plurality of different compounds labeled using the plurality of combinatorial fluorescence energy transfer tags, wherein each different compound is labeled using a tag having a unique fluorescence emission signature. In different embodiments, the compounds are selected from the group consisting of oligonucleotides, oligonucleotide probes, oligonucleotide primers, nucleotides, deoxynucleosides, and antibodies. The invention further provides for the use of the plurality of combinatorial fluorescence energy transfer tags in multi-component analyses.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

I. The Design of Combinatorial Fluorescence Energy Transfer Tags

Background: Optical interactions persist between two chromophores even when they are as far as 80 angstroms apart. The chromophore with high energy absorption is defined as a donor, and the chromophore with lower energy absorption is defined as an acceptor. Fluorescence energy transfer is mediated by a dipole-dipole coupling between the chromophores that results in resonance transfer of excitation energy from an excited donor molecule to an acceptor (Förster, 1965). Förster established that the energy transfer efficiency is proportional to the inverse of the sixth power of the distance between the two chromophores. Fluorescence resonance energy transfer has been used extensively as a spectroscopic ruler for biological structures (Stryer, 1978), and energy transfer-coupled tandem phycobiliprotein conjugates have found wide applications as unique fluorescent labels (Glazer and Stryer, 1983). A set of polycationic heterodimeric fluorophores that exploit energy transfer and have high affinities for double-stranded DNA were also developed, offering advantages over monomeric fluorophores in multiplex fluorescence labeling applications (Benson et al., 1993; Rye et al., 1993). By exploiting fluorescence energy transfer principle, using a common donor and four different acceptors, four sets of ET primers and dideoxynucleotides were constructed that are markedly superior to single dye labels in DNA sequencing, and in multiplex polymerase chain reaction (PCR)-based mapping and sizing protocols (Ju et al., 1995, 1996).

The present application discloses how energy transfer and combinatorial concepts can be used to tune the fluorescence emission signature of fluorescent tags for the development of a large number of combinatorial fluorescence energy transfer (CFET) tags. Representative examples for the construction of the CFET tags and their expected fluorescence signatures are shown in FIG. 10. Three individual fluorescent dyes, 6-carboxyfluorescein (FAM or F), N,N,N',N'-tetramethyl-6-carboxyrhodamine (TAM or T) and Cyanine dye (Cy5 or C) are selected as examples to construct the CFET tags. The fluorescence emission maxima for FAM, TAM and Cy5 are 525 nm, 580 nm and 670 nm, respectively. Chemical moieties used as spacers are selected to construct various CFET tags aimed at conveniently labeling biomolecules and other targets of interest. As shown in FIG. 10, tag 1 is constructed with FAM alone and displays its characteristic fluorescence signature (Nmax=525 nm). With FAM as a donor and TAM as an acceptor, CFET tags 2, 3, 4, and 5 can be constructed by changing the distance "R" between the FAM and TAM chromophores. The rationale is that altering the distance between donor and acceptor changes the energy transfer efficiency, and therefore the ratio of the fluorescence emission intensity of the donor (FAM) and acceptor (TAM).

Similarly, with FAM as a donor and Cy5 as an acceptor, CFET tags 6, 7 and 8 can be generated. With three dyes, with FAM as a donor, TAM as an acceptor for FAM and as a donor for Cy5, which acts as the final acceptor, CFET tags 9 and 10 can be constructed by manipulating distances "R1" and "R2". All the CFET tags can be excited with a single laser source and analyzed by simple detectors capable of capturing the emission signatures from each tag. In other embodiments, more than three dyes can be used.

Figure 1:
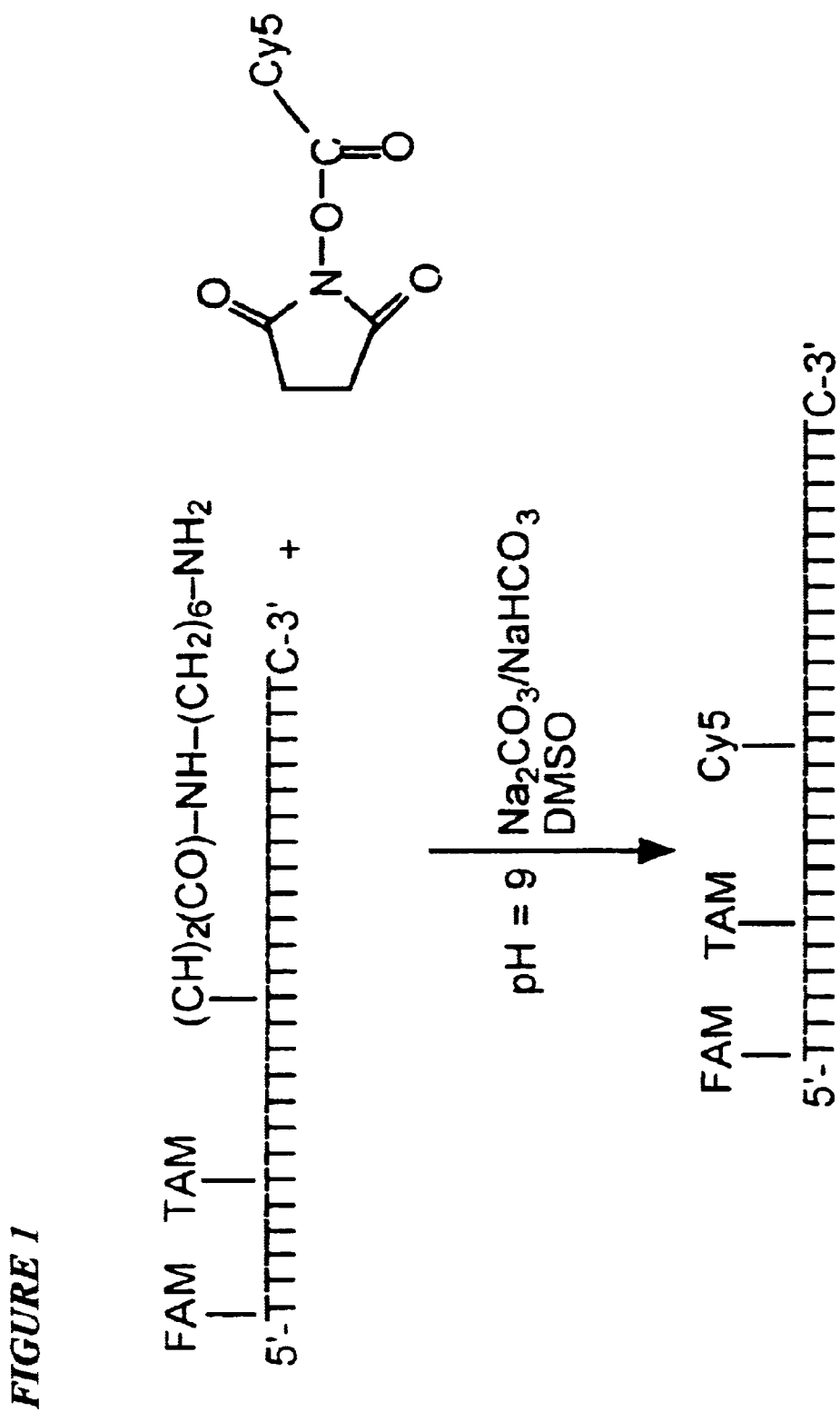
FIG. 1: The synthesis of F-4-T-6-C.

The donor and acceptor fluorescent molecules are separated using convenient chemical moieties as spacers to tune the fluorescence signatures of the CFET tags. Examples of such spacer moieties include id nucleotides, dideoxyribose phosphate, and amino acids. The construction of CFET tags involving three or more different dyes is more challenging, since synthetic procedures need to be designed for introducing the individual dye molecules at specific locations on the spacing backbone. As an example, CFET tags involving three dyes can be constructed using oligonucleotides as spacers. An oligonucleotide with the sequence 5'-TTTTTTTTTTTTTTTTTTTTTTTTTC-3' (SEQ ID NO: 1) was selected as a scaffold to covalently attach FAM, TAM and Cy5. FAM is introduced by using a 6-FAM-dT phosphoramidite, TAM is introduced by using TAM-dT (Glen Research, Sterling, Va.), and a modified T having an amino linker at the C-5 position (Glen Research) is incorporated into the oligonucleotide which is then linked to Cy5-N-Hydroxy succinimide (NHS) ester. The final product is purified by size exclusion chromatography and gel electrophoresis. A representative reaction for the construction of CFET tag F-4-T-6-C (the numbers refer to the number of spacing nucleotides) involving FAM, TAM and Cy5 is shown in FIG. 1. By changing the spacing between FAM and TAM, and TAM and Cy5, two CFET tags F-4-T-6-C and F-7-T-3-C with the fluorescence signatures corresponding to tags 9 and 10 have been constructed as shown in FIG. 2. Shown are the ultraviolet/visible absorption spectrum of F-4-T-6-C (FIG. 2B) as well as the fluorescence emission spectra for F-4-T-6-C and F-7-T-3-C (FIGS. 2C and 2D), with excitation at 488 nm (1x Tris-Borate-Ethylenediaminetetraacetic acid (TBE) solution). The UV/visible spectrum exhibits the characteristic absorption of FAM at 495 nm, TAM at 555 nm and Cy5 at 649 nm (FIG. 2B). The fluorescence emission spectrum of F-4-T-6-C displays a fluorescence signature with Cy5 highest, TAM next and FAM lowest; whereas F-7-T-3-C displays a fluorescence signature with FAM highest, TAM next and Cy5 lowest. The two fluorescence signatures are clearly different, and easily discernible by spectroscopic methods. Here the feasibility of the CFET approach involving three different dyes is clearly demonstrated.

It is evident that one can synthesize broad families of CFET tags. Examples of two synthetic approaches for constructing CFET tags are shown: (1) 1', 2'-dideoxyribose phosphate monomer can be used as a spacer to separate dyes used for labeling oligonucleotide primers, which can be assembled on a DNA synthesizer; (2) a rigid peptide linker can be used to construct a CFET cassette to label any other molecular targets.

The first example is shown in FIG. 3A. A polymer linker (SSS . . . SSSS) formed by 1',2'-dideoxyribose phosphates (S) at the 5' end of the desired primer sequence forms a universal spacer for attaching the ET-coupled fluorophores, thereby producing an ET cassette. The 1',2'-dideoxyribose phosphates can be introduced using 5'-dimethoxytrityl-1',2'-dideoxy ribose-3'-[(2-cyanoethyl)-(N,N-diisopropyl)]-phosphoramidite (dSpacer CE Phosphoramidite, Glen Research, Sterling, Va.). dSpacer CE Phosphoramidite has previously been used to construct DNA sequencing primers (Ju et al., 1996). In this CFET tag construction, FAM is used as a common donor. In a CFET tag consisting of two different fluorescent dyes, either TAM or Cy5 can be used as acceptors; whereas in a CFET tag consisting of three different fluorescent dyes, TAM can also be used as a donor for Cy5. The length of the spacing between each donor/acceptor pair can be changed systematically to achieve the expected fluorescence signatures as shown in FIG. 10. FAM and TAM can be introduced using phosphoramidite FAM-dT and TAM-dT and Cy5 can be introduced to the modified T carrying an amino linker as described above. The use of such spacers is advantageous in several aspects: (i) the spacer will not hybridize to any sequences within the DNA template and therefore false priming is avoided; (ii) the linkage of the spacer maintains the natural nucleic acid phosphate functionality, which avoids possible anomalies in electrophoretic mobility; and (iii) the elimination of the aromatic base groups on the deoxyribose rings in the spacer may reduce the likelihood of fluorescence quenching.

The second synthetic approach requires sophisticated selective synthetic chemistry procedures for the CFET tag construction. As an example, FIG. 3B shows a general scheme for the construction of CFET-deoxyuridine triphosphate (dUTP) using poly-proline (P) peptide as a spacer. The spacing between each donor/acceptor pair can be changed systematically to achieve the expected fluorescence signatures as shown in FIG. 10. FIG. 4 shows a scheme for the synthesis of CFET-dUTP consisting of Fam, Tam and Cy5. Peptide synthesis procedure using tert-butylcarbonyl (t-Boc) chemistry is employed on a peptide synthesizer to construct the scaffold of the desired molecules. Starting with a glycine-resin as C-terminal, a modified proline tagged with FAM (Fam-proline) is coupled to glycine, then proline monomers are added, followed by reacting with another modified proline that has a protected primary amino linker (TFA-NH-proline) for the subsequent incorporation of Tam. Next, proline spacer is again added, followed by reacting with the azido-proline for the subsequent incorporation of Cy5. After cleavage from the resin and removal of the trifluoroacetyl group, compound 1 in FIG. 4 is obtained. Compound 1 reacts with TAM-NHS ester to form compound 2, which will then react with CyS-phosphine (3) to produce compound 4, which has all the three dyes incorporated. Cy5-phosphine (3) can be synthesized using the modified Staudinger reaction developed by Bertozzi (Saxon and Bertozzi, 2000). Conversion of compound 4 to an NHS ester produces 5, which is then coupled to Aminoallyl (AA)-dUTP (Sigma) to generate the final product CFET-dUTP. By varying the number of proline spacers between Fam and Tam, and between Tam and Cy5, a library of CFET-dUTPs with unique fluorescence signatures can be developed. The intermediates 2, 4, 5, and the final products can be purified by high pressure liquid chromatography (HPLC), size exclusion chromatography and gel electrophoresis. The structures of AA-dUTP, Fam-Proline, and NHS esters of TAM and Cy5 are shown in FIG. 5. Brief synthetic schemes for the synthesis of trifluoroacetic (TFA)-NH-proline, Fam-proline, azido-proline and Cy5-phosphine are shown in FIG. 6.

II. Biomedical Applications of Combinatorial Fluorescence Energy Transfer Tags

The ability to sequence DNA accurately and rapidly is revolutionizing biology and medicine. The confluence of the massive Human Genome Project is driving an exponential growth in the development of high throughput genetic analysis technologies. This rapid technological development involving biology, chemistry, computer science, and engineering makes it possible to move from studying genes one by one to approaches which can analyze and compare entire genomes.

Sophisticated techniques have enabled large-scale dissection of genomes. For instance, the development of cloning vectors which can maintain and reproduce large stretches of DNA (up to a million bases) has resulted in clone libraries which span most of the chromosomes from end to end for many of the highly studied organisms including humans—so-called physical maps. Recognizing sequence markers that differ from one individual to another across the human genome has permitted them to be followed in families that harbor genetic diseases. If a marker cosegregates with the disease phenotype, one can be assured that the marker is in the vicinity of the gene responsible for that disease. Automated sequencing methods have made it possible to obtain the complete chemical composition of the genome with unprecedented speed, and computational approaches are beginning to allow annotation of these sequences, identification of the genes and other elements that comprise the chromosomes. Gene expression has moved from the arena of analyzing a few genes at a time by the techniques of Northern blot analysis, to creating vast microarrays of these genes on glass slides or silicon chips (Schena et al. 1995, Chee et al. 1996). Methods for identifying single nucleotide polymorphisms (SNPs) (Chen and Kwok, 1997), DNA-protein and protein-protein interactions (Uetz et al. 2000), and members of metabolic, signal transduction and other pathways are also being developed. All these advances will have the potential to revolutionize medical and clinical research in establishing diagnostic, prognostic or treatment options.

It is noteworthy that many of the genomic techniques mentioned have benefited from the use of novel molecular tags, especially fluorescent dye molecules.

DNA sequencing serves as a good example for evaluating the impact of this technology. Although the ability to obtain DNA sequences originated in the late 1970's with the development of the chemical cleavage approach of Maxam and Gilbert (1977) and the dideoxynucleotide terminator approach of Sanger et al. (1977), it was the latter that was most amenable to automation and fluorescent labeling strategies. In the past 15 years, in rapid succession, the ability to use four dyes in a single sequencing lane, one for each of the four bases in DNA (Smith et al. 1986), the ability to use cycle sequencing with heat stable enzymes (Tabor et al. 1995), the development of energy transfer dyes which produced higher signals (Ju et al., 1995; Lee et al., 1997), and more recently, the ability to obtain long sequence reads in separate capillary tubes instead of adjacent lanes on polyacrylamide slab gels, has made sequencing increasingly robust. Future improvements in sequencing technology, including miniaturization and solid phase approaches, will continue to take advantage of energy transfer (ET) and other novel fluorescent tags (Ju et al., 1997). Investigators are also utilizing ET dyes for investigating gene expression on microarrays (Hacia et al. 1998). All of these approaches are believed to be limited to single pairs of donor and acceptor dyes for each reaction. The CFET approach described herein whereby one, two or more dyes, disposed at varying molecular distances from each other to generate many alternative discrete signatures offers the possibility of obtaining an order of magnitude higher throughput in many of these genomic approaches.

Genetic mutation and chromosome analysis are two examples of the biomedical application of these CFET tags.

Gene mutations play important roles in the development of many human diseases. It has become increasingly apparent that missense mutations (single base changes usually culminating in amino acid changes or introduction of stop codons which lead to truncated proteins), microdeletions and microinsertions (both of which can change the reading frame and also usually lead to protein truncation) can occur at many positions along the length of the responsible gene. A number of studies have sought to identify causative mutations and predisposing polymorphisms for a number of cancers and other diseases. These include chronic lymphocytic leukemia and other blood cancers (Kalachikov et al. 1997; Qu et al. 1998), the long QT syndrome (an ionic disturbance in the heart visible on electrocardiograms and an important risk factor for sudden cardiac death), breast cancer (Fischer et al. 1996), the rare ICF syndrome (immune deficiency/centromeric instability/facial anomalies) (Xu et al. 1999), and more recently such complex disorders such as asthma and diabetes.

With the exception of the types of small mutations described above and single nucleotide polymorphisms that occur, on average, every 1000 nucleotides, the 6 billion nucleotide pairs that make up the diploid human genome are largely identical from individual to individual. Nonetheless, large deletions, amplifications and rearrangements do occur, and such chromosomal anomalies are often associated with serious and life-threatening diseases. The best known example is probably the third copy of chromosome 21 in individuals with Down syndrome, but many other chromosomal translocations and macrodeletions are associated with cancer and other disease syndromes. If one is able to mark the positions along chromosomes with identifiable "color-coded" probes, it should be possible to easily detect such large-scale changes in chromosomal geography. In fact, the field of chromosome painting (multicolor fluorescence in situ hybridization (M-FISH) has been used for just such analyses (Speicher et al. 1996). A larger set of more readily separable CFET tag signatures might greatly aid in this enterprise. The established chromosome painting techniques require appropriate mixing of the different dyes prior to labeling, and so are used almost exclusively for labeling whole chromosomes.

III. CFET Tags for Multiplex Gene Mutation Detection Using Ligase Chain Reaction Ligase chain reaction (LCR) is a procedure for genetic mutation analysis using ligase and a pair of oligonucleotides (Eggerding, 1995; Wu and Wallace, 1989; Landegren et al., 1988). Briefly, it is based on the fact that two adjacent oligonucleotides can only be ligated if the adjoining bases are complementary to the template strand. If there is a single base difference within two bases of the join site, ligation will not occur. Pairs of oligonucleotides are designed spanning the ligation site on the template DNA, including one harboring either the wild-type or mutated base. In the usual procedure, one of the oligonucleotides is radiolabeled at the phosphate group at its 5' end. Following the ligase chain reaction, which involves multiple rounds of denaturing, primer annealing and ligation, one can separate the products from the substrates on polyacrylamide gels. The procedure can be modified using single stranded DNA template as shown in FIG. 7 for testing using the CFET tags. Primer pairs are generated surrounding a base that can be mutated. For example, the template may contain a T (wild-type, wt) or C (mutated, mut) at the relevant position. The wt primers are complementary to the wt template at every position. The primer on the right side of FIG. 7A is labeled with CFET tag 1 to yield a specific fluorescent signature. The mutation-specific primer, two bases longer than its wild-type analog, is complementary to every position of the mutated template. This primer is labeled with CFET tag 2 displaying another unique fluorescent signature. A common 20 base pair primer will be used on the other side of the ligation site. In cases where ligation does not occur, because a wild-type oligonucleotide was used with a mutated template sequence, or a mutated oligonucleotide was used with a wild-type template sequence, the only fluorescent band on the acrylamide gel will be the size of the tagged primer. In contrast, if there is no mismatch at the ligation junction, two fluorescent bands, one the size of the primer and one the size of the joined primers will form. Following ligase chain reaction, the left and right primer will be ligated only if they are completely complementary to the template. Thus, with a wt template, only a 40 base product will result, and only a 42 base product will result from a mut template as shown in FIG. 7B. By virtue of the unique fluorescence emission signatures of the CFET tags, it is possible to display the products of several mutation positions simultaneously, each labeled with a different CFET Tag. The ligated products can be separated and analyzed in a single gel lane. In order to accomplish this, the multiplex set of oligonucleotides that contain the potentially mutated position can be 5'-end labeled, each with a specific CFET tag. For example, one can test four different mutation sites using eight distinct CFET tags.

As shown in Table 1, eight primers labeled with eight unique CFET tags (1, 2, 3, 4, 5, 6, 9, and 10 of FIG. 10) can be constructed as shown in the general labeling scheme in FIG. 3A using 1',2'-dideoxysugar phosphate (S) as spacers. For this set of CFET tag constructs, FAM is used as a common donor, and TAM and/or Cy5 as acceptors. The length of the spacing between each donor/acceptor pair, (S)m and (S)n, can be changed systematically to achieve the expected fluorescence signatures as depicted in FIG. 10. FAM and TAM can be introduced using FAM-dT and TAM-dT phosphoramidites and Cy5 can be introduced to the modified T carrying an amino linker as described above.

The system can be tested, for example, by synthesizing single stranded DNA templates mimicking known single base mutations in exon 20 of the retinoblastoma susceptibility (Rb1) gene (Schubert et al. 1994, Lohmann 1999). The sequences of two sets of synthetic templates (wt and mut) which can be used in the analysis are shown in Table 2. The sequence of the potential mutation positions is shown in bold-face as "A", "C", "G" and "T". Primer sets 1 and 2 in Table 1 are used for the testing of both wild type and mutated base positions of Template A, respectively; while primer sets 3 and 4 are for testing both wild type and mutated base positions of Template B, respectively. To maximize the number of samples that can be detected on a polyacrylamide gel, the primers surrounding each "mutated" position can be designed to be a unique length as shown in FIG. 8. For example, the two CFET labeled oligonucleotides (one for the wild-type gene and one for the mutated gene) surrounding mutation position 1 are 20 and 22 bases long, respectively, and the unlabeled common primer is 20 bases long. Any resulting ligation product will be either 40 or 42 bases long. Likewise, for mutation position 2, 24 and 26 base labeled oligonucleotides can be constructed, as well as a different 20 base common primer, leading to ligation products of either 44 or 46 bases. More primers can, of course, be generated by making the sizing increment one base instead of two bases for each different mutation, or creating a second set of labeled primers whose ligation products run between 80 and 98 base pairs, between 120 and 138 base pairs, etc. Since single base pair resolution up to the length of 400 bp DNA fragments is easily achieved in polyacrylamide gel electrophoresis, the ligated products can be readily resolved in such standard fluorescent gel systems. Furthermore, the advantage of being able to clearly distinguish the products based on their fluorescent signatures, as well as size, makes this assay extremely powerful. Expected gel electrophoresis results for this multiplex testing system are shown on the right side of FIG. 8. Here, template collection 1 is seen to contain only wt sequences. In contrast, template pool 2 contains one template with a mutation at position 2 and a heterozygote genotype at position 4.

TABLE 1

Eight primers used for multiplex mutation detection

| Primer 1L: (SEQ ID NO: 2) | 3'-ttaaaaagaataagggtgtc-5' |
|---|---|
| Primer 1R wt: (SEQ ID NO: 3) | 3-Acatagccgatcggatagag-5'-CFET1 |
| Primer 1R mut: (SEQ ID NO: 4) | 3'-Tcatagccgatcggatagaggc-5'-CFET2 |
| Primer 2L: (SEQ ID NO: 5) | 3'-acatagccgatcggatagag-5' |
| Primer 2R wt: (SEQ ID NO: 6) | 3'-Gccgatttatgtgaaacacttgcg-5'-CFET3 |
| Primer 2R mut: (SEQ ID NO: 7) | 3'-Accgtatttatgtgaaacacttgcgga-5'-CFET4 |
| Primer 3L: (SEQ ID NO: 8) | 3'-cggaagacagactcgtgggt-5' |
| Primer 3R wt: (SEQ ID NO: 9) | 3'-Cttaatcttgtatagtagacctgggaaa-5'-CFET5 |
| Primer 3R mut: (SEQ ID NO: 10) | 3'-Attaatcttgtatagtagacctgggaaaag-5'-CFET6 |
| Primer 4L: (SEQ ID NO: 11) | 3'-atagtagacctgggaaaagg-5' |
| Primer 4R wt: (SEQ ID NO: 12) | 3'-Tcgtgtgggacgtcttactcatacttgagt-5'-CFET7 |
| Primer 4R mut: (SEQ ID NO: 13) | 3'Gcgtgtgggacgtcttactcatacttgagtac-5'-CFET8 |

TABLE 2

The sequence of the two sets of synthetic templates (wt and mut)

Template A:

5'-gtaaaaatgactaattttcttattcccacagTgtatcggctagcctatc tcCggctaaatacactttgtgaacgccttctgtctgagcacccagaatta-3' (wild type) (SEQ ID NO: 14)
5'-gtaaaaatgactaattttcttattcccacagAgtatcggctagcctatc tcTggctaaatacactttgtgaacgccttctgtctgagcacccagaatta-3' (mutated) (SEQ ID NO: 15)

Template B:

5'-tacactttgtgaacgccttctgtctgagcacccaGaattagaacatatca tctggacccttttccAgcacacccctgcagaatgagtatgaactcatgaga-3' (wild type) (SEQ ID NO: 16)
5'-tacactttgtgaacgccttctgtctgagcacccaTaattagaacatatca tctggacccttttccCgcacacccctgcagaatgagtatgaactcatgaga-3' (mutated) (SEQ ID NO: 17)

IV. CFET Tag Labeled Probes for Chromosome-wide Analysis

Probes can be generated using a random primed labeling method to incorporate CFET-dUTP into chromosome-specific DNA molecules or cosmids disposed along the length of a given chromosome. Metaphase spreads of fresh cells or deparaffinized material can be prepared by standard methodologies, and the tagged probes can be hybridized to the chromosomes. Bulky ET dyes consisting of two individual fluorescent molecules, as well as dyes with a long linker, have been attached to deoxynucleotides (dNTPs) and dideoxynucleotides (ddNTPs) which have been shown to be good substrates for DNA polymerase (Rosenblum et al. 1997, Zhu et al. 1994). Thus, the CFET-dUTP should be able to be incorporated into the growing strand by the polymerase reaction. In the actual random priming reaction, the ratio of regular deoxythymine triphosphate (dTTP) and CFET-dUTP can be adjusted, so that only a small portion of CFET-dUTP will be incorporated into the growing chain, just enough to be detected by the optical method.

Numerical and structural chromosome rearrangements are a major cause of human mortality and morbidity. Aneuploidy of whole chromosomes accounts for at least 50% of early embryonic lethality, and also leads to severe patterns of congenital malformation such as Down syndrome. Segmental aneuploidies due to deletions and duplications also lead to malformation syndromes, as well as being associated with many types of cancer.

Traditional cytogenetic analysis is hampered by problems of resolution and interpretation inherent in standard banding analysis. In the last decade the use of fluorescent labeled DNA probes on chromosome preparations as well as on interphase nuclei has greatly improved the resolution and accuracy of cytogenetic diagnosis. Microdeletions and amplifications too small to be visible under the light microscope by banding can now be visualized using chromosome and region specific fluorescently labeled probes. Multiplexing this system is possible using combinations of probes labeled with different fluors. Sets of up to five differently labeled probes have been used for diagnostic purposes on interphase nuclei to determine aneuploidy in prenatal samples (Munne et al. 1998). M-FISH and Spectral Karyotyping use a combinatorial approach of five dyes to "paint" all 23 pairs of human chromosomes so they can be distinguished using computerized image software (Schrock et al. 1996, Speicher et al. 1996). However, these established techniques require careful mixing of dyes in controlled ratios. Quality control is often a problem, and the commercially available probes are very expensive.

CFET Tags are expected to have a substantial advantage over currently available dye sets. It should be possible to generate a larger number of CFET tag sets, reducing the need for a combinatorial approach. Quality control is also likely to be easier, since each probe needs to be labeled with only one tag, and probe sets can be mixed in equal quantities to produce multicolor FISH reagents.

CFET Tags for example could be used both for the detection of aneuploidy in interphase nuclei, and for the detection of submicroscopic chromosomal deletions and amplifications. For aneuploidy detection, for example, a set of eight different CFET tag labeled probes can be prepared, each specific for one of the chromosomes most commonly involved in aneuploidy in either embryonic losses or birth defects (chromosomes 13, 15, 16, 18, 21, 22, X and Y).

A schematic of a procedure for comprehensive chromosome-wide analysis for gain or loss of genetic material is shown in FIG. 9. In the example, eight probes each labeled with a CFET-dUTP that emits a unique fluorescence signature are hybridized along a chromosome in eight separate locations. The normal chromosome A will display eight unique fluorescence signatures of each probe in a defined order. A loss of fluorescence signature "2" in chromosome B will indicate the deletion of the complementary sequence of probe 2. Whereas, in chromosome C, the appearance of two signatures of "3" will indicate the expansion of the complementary sequences for probe 3.

Standard sets of cosmid and BisAcryloylCystamine (BAC) markers at 2–3 Mb intervals along the chromosomes are being developed in several laboratories, including a National Cancer Institute sponsored project, the Cancer Chromosome Aberration Project (CCAP). Sets of differentially CFET-labeled ordered probes specific for particular chromosomal regions can be prepared. Using FISH, one can then determine the limits of suspected or known deletions.

V. Use of CFET Tags In Other Multi-Component Analyses

The CFET tags with unique fluorescence signatures which are disclosed in the present application will have utility in other applications involving multi component analysis in addition to those disclosed above. Additional applications include, but are not limited to, multiplex assays including binding assays and immuno assays, detection of microbial pathogens, monitoring multiple biomolecular reactions, screening of drugs or compounds, epitope mapping, allergy screening, and use with organic compounds and in material science. For example, multiple reactions or interactions can be measured simultaneously, where multiple CFET tags, each with a different fluorescence signature, are used to label the different reactants which could include, for example, antibodies, antigens, ligands, or substrates. Examples include antibody-antigen and receptor-ligand binding. In further examples, different reactants can be coupled to microspheres.

References

Benson, S. C., Mathies, R. A. & Glazer, A. N. (1993). Heterodimeric DNA-binding dyes designed for energy transfer: stability and applications of the DNA complexes. *Nucleic Acids Res.* 21: 5720–5726.

Benson, S. C., Singh, P. & Glazer, A. N. (1993). Heterodimeric DNA-binding dyes designed for energy transfer: synthesis and spectroscopic properties. *Nucleic Acids Res.* 21: 5727–5735.

Chee, M., Yang, R., Hubbell, E., Berno, A., Huang, X. C., Stern, D., Winkler, J., Lockhart, D. J., Morris, M. S., Fodor, S. P. (1996). Accessing genetic information with high-density DNA arrays. *Science.* 274: 610–614.

Chen, X and Kwok, P Y. (1997) Template-directed dye-terminator incorporation (TDI) assay: a homogeneous DNA diagnostic method based on fluorescence resonance energy transfer *Nucl. Acids. Res.* 25: 347–353.

Eggerding F A (1995) A one-step coupled amplification and oligonucleotide ligation procedure for multiplex genetic typing. *PCR Methods Appl.* 4: 337–345.

Fischer, S. G., Cayanais, E., de Fatima Bonaldo, M., Bowcock, A. M., Deaven, L. L., Edelman, I. S., Gallardo, T., Kalachikov, S., Lawton, L., Longmire, J. L., Lovett, M., Osborne-Lawrence, S., Rothstein, R., Russo, J. J., Soares, M. B., Sunjevaric, I., Venkatraj, V. S., Warburton, D., Zhang, P. and Efstratiadis, A. (1996) A high-resolution annotated physical map of the human chromosome 13q12-13 region containing the breast cancer susceptibility locus BRCA2. *Proc. Natl. Acad. Sci. U.S.A.* 93: 690–694.

Forster, T. (1965) In: Modern Quantum Chemistry, Istanbul Lectures, Part III. Sinanoglu, O. (editor), Academic Press, New York, pp 93–137.

Glazer, A. N., Stryer, L. (1983) Fluorescent tandem phycobiliprotein conjugates. Emission wavelength shifting by energy transfer. *Biophys. J.* 43(3):383–386.

Hacia J. G., Edgemon K., Sun B., Stern D., Fodor S. A., Collins F. S. (1998). Two Color Hybridization Analysis Using High Density Oligonuleotide Arrays and Energy Transfer Dyes *Nucleic Acids Research* 15; 26: 3865–6.

Ju, J., Glazer, A. N. & Mathies, R. A. (1996) Cassette labeling for facile construction of energy transfer fluorescent primers. *Nucleic Acids Res.* 24, 1144–1148.

Ju J, Glazer A N and Mathies R A (1996) Energy transfer primers: A new fluorescence labeling paradigm for DNA sequencing and analysis. *Nature Medicine* 2: 246–249.

Ju J, Ruan C, Fuller C W, Glazer A N and Mathies R A (1995) Energy transfer fluorescent dye-labeled primers for DNA sequencing and analysis. *Proc. Natl. Acad. Sci. USA* 92: 4347–4351.

Ju J, Yan H, Zaro M, Doctolero M, Goralski T, Konrad K, Lachenmeier E and Cathcart R (1997) DNA sequencing with solid phase captureable terminators. *Microb. Comp. Genomics* 2: 223.

Kalachikov, S. et al. (1997) Cloning and gene mapping of the chromosome 13q14 region deleted in chronic lymphocytic leukemia. *Genomics* 42(3): 369–377.

Landegren U, Kaiser R, Sanders J and Hood L (1988) A ligase-mediated gene detection technique. *Science* 241: 1077–1080.

Lee L G, Spurgeon S L, Heiner C R, Benson S C, Rosenblum B B, Menchen S M, Graham R J, Constantinescu A, Upadhya K G and Cassel J M (1997) New energy transfer dyes for DNA sequencing. *Nucleic Acids Res.* 25: 2816–2822.

Lohmann D R (1999) RB1 gene mutations in retinoblastoma. *Hum Mutat.* 14: 283–288.

Maxam A M and Gilbert W (1977) A new method for sequencing DNA. *Proc Natl. Acad. Sci. USA* 74: 560–564.

Munne S, Magli C, Bahce M, Fung J, Legator M, Morrison L, Cohert J, Gianaroli. (1998) Preimplantation diagnosis of the aneuploidies most commonly found in spontaneous abortions and live births: XY, 13, 14, 15, 16, 18, 21, 22. *Prenat Diagn.* 18: 1459–66.

Qu, X., Hauptschein, R. S., Rzhetsky, A., Scotto, L., Chien, M., Ye, X., Frigeri, F., Rao, P. H., Pasqualucci, L., Gamberi, B., Zhang, P., Chaganti, R. S. K., Dalla-Favera, R. and Russo, J. J. (1998) Analysis of a 69 kb contiguous genomic sequence at a putative tumor suppressor gene locus on human chromosome 6q27. *DNA Seq.* 9: 189–204.

Rosenblum, B. B., Lee, L. G., Spurgeon, S. L., Khan, S. H., Menchen, S. M., Heiner, C. R., Chen, S. M. (1997). New dye-labeled terminators for improved DNA sequencing patterns. *Nucleic Acids Res* 25: 4500–4.

Rye, H. S., Drees, B. L., Nelson, H. C. M. & Glazer, A. N. (1993). Stable fluorescent dye-DNA complexes in high sensitivity detection of protein-DNA interactions. Application to heat shock transcription factor. *J. Biol. Chem.* 268: 25229–25238.

Sanger F, Nickeln S and Coulson A R (1977) DNA sequencing with chain-terminating inhibitors. *Proc. Natl. Acad. Sci. USA* 74: 5463–5467.

Saxon E and Bertozzi C R (2000), Cell Surface Engineering by a Modified Staudinger Reaction. *Science,* 287: 2007–2010.

Schena, M., Shalon D., Davis, R. and Brown P. O. (1995) Quantitative monitoring of gene expression patterns with a cDNA microarray. *Science* 270: 467–470.

Schrock E, du Manoir S, Veldman T, Schoell B, Wienberg J, Ferguson-Smith M A, Ning Y, Ledbetter D H, Bar-Am I, Soenksen D, Garini Yand Ried T (1996) Multicolor spectral karyotyping of human chromosomes. *Science* 273: 494–497.

Schubert E L, Hansen M F and Strong L C (1994). The retinoblastoma gene and its significance. *Ann Med.* 26: 177–184.

Smith, L. M., Sanders, J. Z., Kaiser, R. J., Hughes, P., Dodd, C., Connell, C. R., Heiner, C., Kent, S. B. H. and Hood, L. E. (1986). Fluorescence detection in automated DNA sequencing analysis. *Nature.* 321: 674–679.

Speicher M R, Ballard S G and Ward D C (1996) Karyotyping human chromosomes by combinatorial multi-fluor FISH. *Nature Genet.* 12: 368–375.

Stryer, L. (1978) Fluorescence energy transfer as a spectroscopic ruler. *Annu. Rev. Biochem.* 47: 819–846.

Tabor, S. & Richardson, C. C. A single residue in DNA polymerases of the *Escherichia coli* DNA polymerase I family is critical for distinguishing between deoxy- and dideoxyribonucleotides. 1995. *Proc. Natl. Acad. Sci. U.S.A.* 92: 6339–6343.

Uetz, et al; and S. Fields (2000) A comprehensive analysis of protein-protein interactions in Saccharomyces cerevisiae. *Nature* 403 (Number 6770) 623–627.

Vogel. (1989) Textbook Of Practical Organic Chemistry, Fifth Edition, Addison Wesley Longman, Harlow, U. K.

Wu D Y and Wallace R B (1989) The ligation amplification reaction (LAR): Amplification of specific DNA sequences using sequential rounds of template-dependent ligation. *Genomics* 4: 560–569.

Xu, G.-L., Bestor, T. H., Bourc'his, D., Hsieh, C-L., Tommerup, N., Bugge, M., Hulten, M., Qu, X., Russo, J. J. and Viegas-Péquignot, E. (1999) Chromosome instability and immunodeficiency syndrome caused by mutations in a DNA methyltransferase gene. *Nature* 402: 187–191.

Zhu Z ; Chao J ; Yu H ; Waggoner A S (1994). Directly labeled DNA probes using fluorescent nucleotides with different length linkers. *Nucleic Acids Res*, 22: 3418–22.

What is claimed is:

1. A combinatorial fluorescence energy transfer tag which comprises the structure:

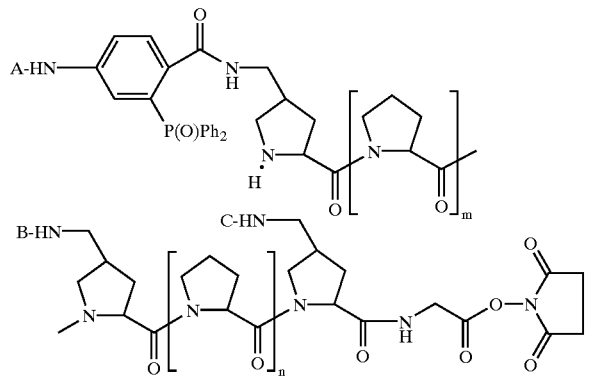

wherein A, B, and C represent different fluorescent molecules which comprise one or more energy transfer donor and one or more energy transfer acceptor, wherein m and n represent any integer greater than or equal to one, and wherein fluorescent molecules A, B, and C are separated from each other to produce a unique fluorescence emission signature.

2. The combinatorial fluorescence energy transfer tag of claim 1, wherein the fluorescent molecules are selected from the group consisting of 6-carboxyfluorescein, N,N,N',N'-tetramethyl-6-carboxyrhodamine, and cyanine.

3. An oligonucleotide primer labeled using the combinatorial fluorescence energy transfer tag of claim 1.

* * * * *